United States Patent [19]
Moorehead

[11] Patent Number: 5,456,102
[45] Date of Patent: Oct. 10, 1995

[54] METHOD AND APPARATUS FOR PARTICLE COUNTING AND COUNTER CALIBRATION

[76] Inventor: Jack Moorehead, 5355 Mira Sorrento Pl., Ste. 100, San Diego, Calif. 92121

[21] Appl. No.: 33,823

[22] Filed: Mar. 19, 1993

[51] Int. Cl.$^6$ .................................................. G01N 15/00
[52] U.S. Cl. .............................. 73/3; 73/1 G; 73/53.07; 73/861.04; 356/335
[58] Field of Search .............................. 73/16, 3, 53.07, 73/61.42, 61.48, 61.69, 861.04; 356/335, 336, 337, 338, 436, 437, 438, 439, 441, 442

[56] References Cited

U.S. PATENT DOCUMENTS

| | | | |
|---|---|---|---|
| 3,520,610 | 7/1970 | Parrent, Jr. et al. | 356/335 |
| 3,952,579 | 4/1976 | Nakajima | 73/61.69 |
| 4,194,391 | 3/1980 | Rosenberger | 73/61.69 |
| 4,519,257 | 5/1985 | Simpkins | 73/861.04 |
| 4,581,942 | 4/1986 | Ogura et al. | 73/861.04 |
| 4,806,015 | 2/1989 | Cottingham | 356/335 |
| 4,850,707 | 7/1989 | Bowen et al. | 356/336 |
| 5,170,150 | 12/1992 | Austin et al. | 356/338 |
| 5,315,115 | 5/1994 | Gerger | 356/336 |
| 5,316,983 | 5/1994 | Fujimori et al. | 356/335 |

FOREIGN PATENT DOCUMENTS

| | | | |
|---|---|---|---|
| 2517059 | 5/1983 | France | 73/861.04 |
| 60-11375A | 1/1994 | Japan | 73/861.04 |

Primary Examiner—Richard Chilcot
Assistant Examiner—George M. Dombroske
Attorney, Agent, or Firm—John R. Duncan; Frank D. Gilliam; Donn K. Harms

[57] ABSTRACT

A system for counting particles entrained in a flowing fluid and for automatically calibrating the counting system is disclosed. A conduct through which a fluid carrying particles flows has a transparent section. A narrow light beam, such as a laser light beam, is passed through the transparent section to a detector, such as a photodiode, that detects light scattered by the particles. The scattering pattern is useful in counting the flowing particles and measuring other particle characteristics, such as size. The measurement system can be calibrated by passing the light beam through a transparent slide bearing a standard particle array to a detector, either the measurement detector or a second detector. The slide is moved at the same rate as the fluid flows, so that the scattering produced by the standard array is useful in calibrating the measurement of the flowing particles in a conventional manner. The calibration may be accomplished by deflecting, such as with a movable mirror, the light beam through the moving slide to a second detector or the body containing the conduit can be moved out of the way so that the slide can be moved across the original light path. A multiple solenoid valve may be provided to selectively direct the particle bearing fluid through the conduit, direct reverse flow of clean water or a gas, such as air, through the conduit to clean the conduit or remove any particle contamination or jams.

29 Claims, 3 Drawing Sheets

5,456,102

METHOD AND APPARATUS FOR PARTICLE COUNTING AND COUNTER CALIBRATION

BACKGROUND OF THE INVENTION

This invention relates in general to apparatus for measuring physical characteristics, such as the number of particles, of a flowing fluid stream and more particularly, to such apparatus which includes automatic calibration and rapid cleaning capabilities.

The counting, sizing and analysis of very small particles entrained in a flowing fluid stream is important in a number of different fields. Determining the efficiency of filters used with drinking water, evaluating contamination, such as by Giardia cysts, in a fluid stream, measuring biological particles in medical cytometers, etc., all require measurement of physical characteristics of the particles, such as the number and size of particles present.

Early methods included flowing the fluid between electrodes which have an imposed current such as is described by Coulter in U.S. Pat. No. 2,656,508 and by Groves et al in U.S. Pat. No. 4,298,836. Particles moving between the electrodes change the impedance of the sensing zone, which can be detected and correlated to particle characteristics. While this system and later variations are effective in many cases, typically in the analysis of biological cells, in general calibration is difficult, not all particle compositions can be effectively analyzed and the electrical system is complex.

Other apparatus which is intended for measuring particles labeled with fluorescent dyes use auto-fluorescent microbeads to calibrate the apparatus, as described in U.S. Pat. No. 5,093,234. The calibration method, however, is cumbersome and time consuming and limited in the types of particles that can be analyzed. Hogg et al in U.S. Pat. No. 4,286,876 describe a particle detection system in which particles, such as white blood cells, are passed through a sensing zone one-by-one. A beam of light is directed through the sensing zone, with photodetectors opposite the light source positioned to detect light scattered by each particle as it traverses the zone. With one light source and a single detector, identification of the particle is described as inefficient, complex and expensive. With a complex array of light sources and detectors, effectiveness improves but the system is still not capable of processing a stream of multiple particles.

Prior apparatus for analyzing particles entrained in fluid streams further have difficulty where there are large number of particles both in the analysis and in avoiding contamination of the analysis device, such as the window through which the stream is observed, to the point where clogging of the stream conduit may occur. Complex systems, such as that described by Simpson et al. in U.S. Pat. No. 4,220,621, have been designed for backwashing mixed fluids from a sampling probe. These systems are complex, not fully effective, and are generally not suitable for periodically cleaning an observation section of a conduit through which a continuous stream flows.

Thus, there is a continuing need for improved devices for measuring physical characteristics of multiple particles in a flowing fluid stream, typically continuously counting the number of particles in the stream. The need remains for a rapid, effective measurement method and apparatus which include the ability to rapidly and accurately calibrate the apparatus on a periodic schedule and which can be automatically cleaned on a regular schedule.

SUMMARY OF THE INVENTION

The above-noted problems are overcome, and needs met, by an apparatus and method for determining physical characteristics, such as the concentration, of particles in a flowing fluid stream which basically includes a conduit through which the fluid flows, the conduit having a transparent section through which a narrow light beam is directed. A detector adjacent to the transparent section detects light scattered by the particles. The scatter pattern obtained is representative of the number of particles in the fluid and of other characteristics such as particle size. The measurement system is calibrated by passing the light beam through a transparent slide bearing a standard particle array, producing a standard scatter pattern against which the measured pattern can be compared.

Since particles contaminating the sides of the transparent conduit section may distort measurements, an arrangement is provided for reversing flow through that section, preferably using clean fluid, and/or for directing a flow of gas, such as air, through the conduit to clear any particle jams and remove surface contamination.

In a first embodiment, calibration is accomplished by moving a reflecting surface into the light beam before the conduit section, and reflecting it through the slide and standard particle array to a second photodetector to obtain the standard scatter pattern. For optimum calibration accuracy, the transparent slide is moved through the calibration light beam at a rate substantially equal to the rate of fluid flow through the conduit during testing.

While calibration is being accomplished, cleaning of the conduit with a reverse flow of clean fluid or gas may be accomplished.

In a second embodiment, the body which contains the conduit transparent section is moved out of the beam path and a transparent slide bearing the standard particle array is moved into the optical path, with the standard scattering pattern being detected by the measurement detector. Preferably, the transparent slide is attached to the body and the body and slide are moved so that the slide moves across the light beam at the same rate that fluid flows through the conduit during testing.

This system is particularly well adapted to counting the number of solid particles and the sizes of the particles flowing in a water stream, such as water that has passed though a filter to monitor the efficiency of the filter or to monitor particle content in a waste water stream or the like. Particles in the filtered water stream can be counted and sized, then unfiltered water can be periodically passed through the device and particles counted and sized to determine filter efficiency. This apparatus and method are advantageous in providing a simple, reliable manner of continuously monitoring particle count and size in a flowing stream, interrupted only periodically for a short recalibration and cleaning cycle.

BRIEF DESCRIPTION OF THE DRAWING

Details of the invention, and of certain preferred embodiments thereof, will be further understood upon reference to the drawing, wherein.

DETAILED DESCRIPTION OF PREFERRED EMBODIMENTS

Figure 1:
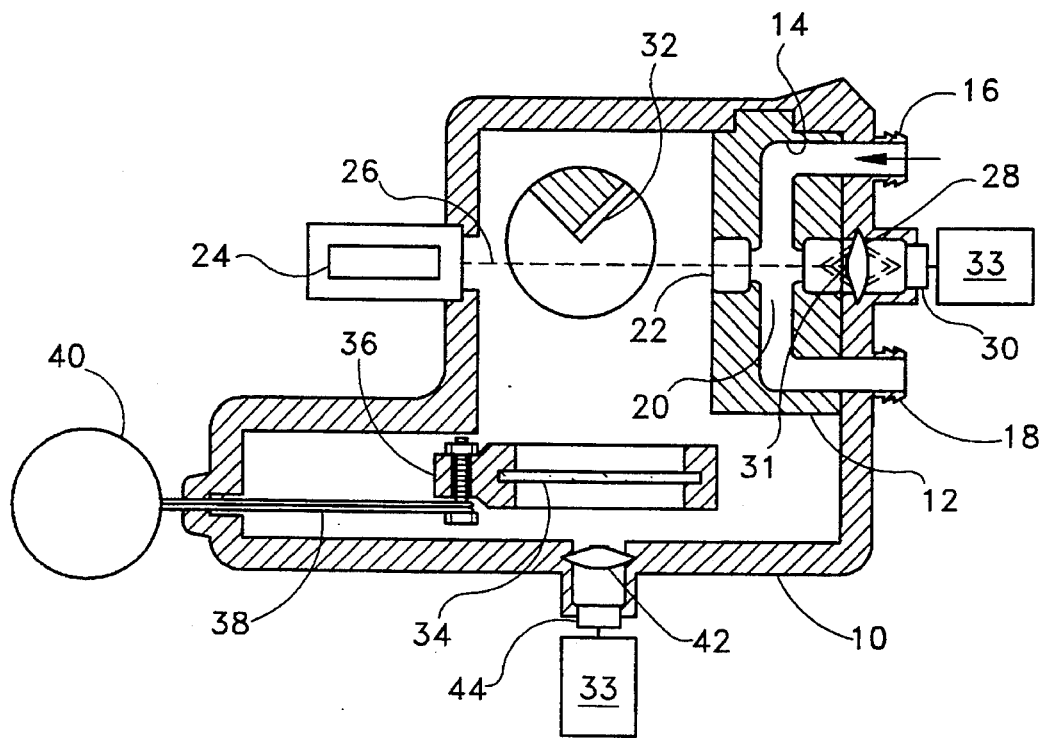
FIG. 1 is a schematic section view through a first embodiment of the apparatus of this invention during particle measurement.

Referring to FIG. 1, there is seen a housing 10 containing a body 12 through which a tubular conduit 14 runs. Conduit 14 includes two connections 16 and 18 (either of which can serve as an inlet and the other as an outlet, depending on flow direction) and a transparent center section 20. Preferably transparent center section 18 is formed through a block 22 of transparent aluminum oxide in the form known as corundum or synthetic sapphire because of the high strength and transparency of that material.

A source 24 of a narrow beam 26 of light, typically a laser, is positioned on housing 10 opposite transparent section 18, so that light beam 26 can pass through the conduit through a condensing lens 28 to a light detector 30, typically a photodiode. A small, opaque laser beam trap 31 is placed at the center of lens 28 to prevent light beam 26 from directly reaching light detector 30. Only scattered light should reach the detector. Any suitable conventional photodiodes may be used. Any suitable laser or other suitable light source may be used. Laser light sources are preferred because of the narrow coherent beams of high intensity monochromatic light produced thereby. When a fluid such as water, carrying a number of solid particles passes through conduit 14, light beam 18 is scattered, condensed by lens 28 and strikes photo detector 30 in a pattern characteristic of particle properties such as number and size of particles. The patterns produced can be compared to patterns produced by particles of known concentrations, sizes, etc. to determine those characteristics.

Since various factors can change over time, such as light beam intensity it is desirable to calibrate the system at regular intervals. In order to calibrate the system, a movable mirror 32 can be moved from the position shown in FIG. 1 with mirror 32 out of the path of light beam 26 to the position shown in FIG. 2, where light beam 26 is deflected to pass through a transparent slide 34 bearing a standard array of particles. Such standard slides are commercially available with various particle sizes and numbers. Such standards are described, for example, by Vogt et al. in U.S. Pat. No. 5,084,394 and Yonemura in U.S. Pat. No. 5,123,738. A preferred standard uses ceramic microbeads imbedded in transparent aluminum oxide (synthetic sapphire).

Slide 34 is held in a mounting 36 supported on a rod 38 connected to a solenoid 40. Solenoid 40 is preferably adjustable to pull slide 34 across beam 26 at a rate substantially equal to the rate at which fluid flows through conduit 14. Such solenoids are commercially available.

Light passing through slide 34 is scattered by the particles therein, condensed by condensing lens 42 and reach photo detector 44 as a characteristic pattern. Preferably, photo detector 44 is a photodiode substantially identical with that at photo detector 30. The patterns produced using standard slide 34 can be used manually or by a computer 33 as a basis for comparison with those obtained from photo detector 30.

Figure 2:
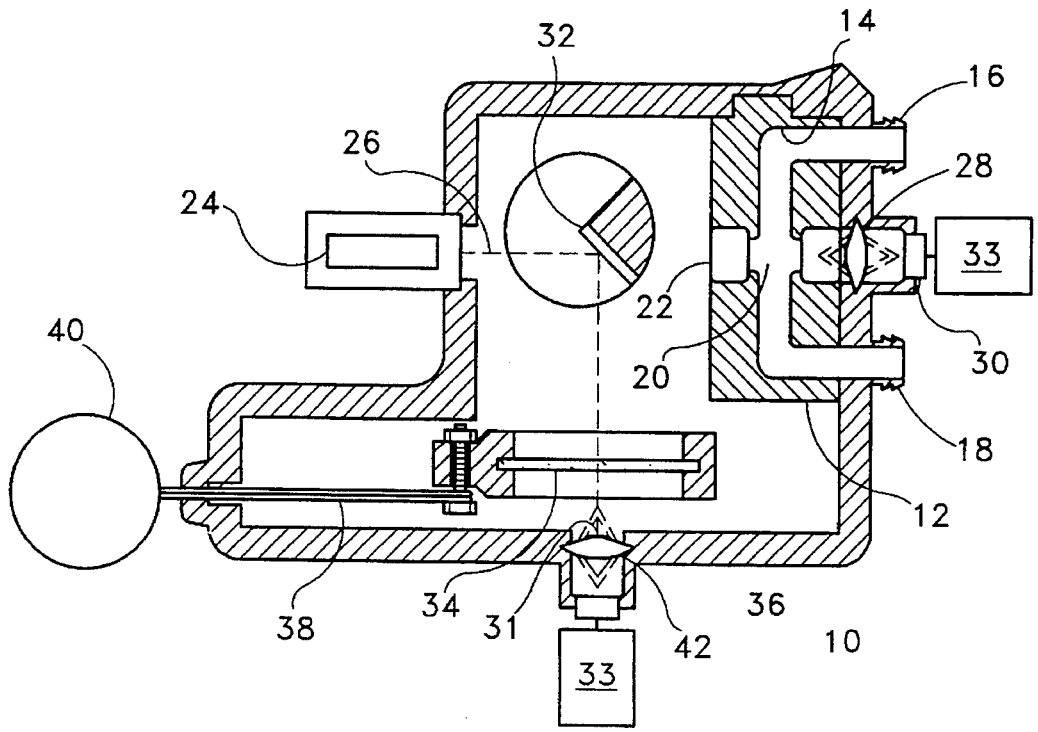
FIG. 2 is a schematic section view through the embodiment of FIG. 1 during system calibration.

While the mirror is in the calibration position shown in FIG. 2, liquid or air may be back flowed through conduit 14, as detailed in conjunction with the description of FIGS. 5 and 6, below.

Figure 3:
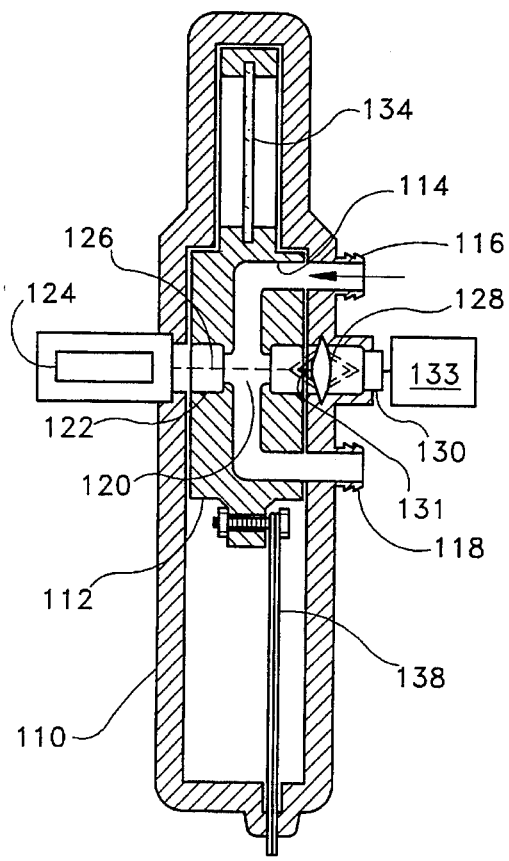
FIG. 3 is a schematic section view through a second embodiment of the apparatus of this invention during particle measurement.
Figure 4:
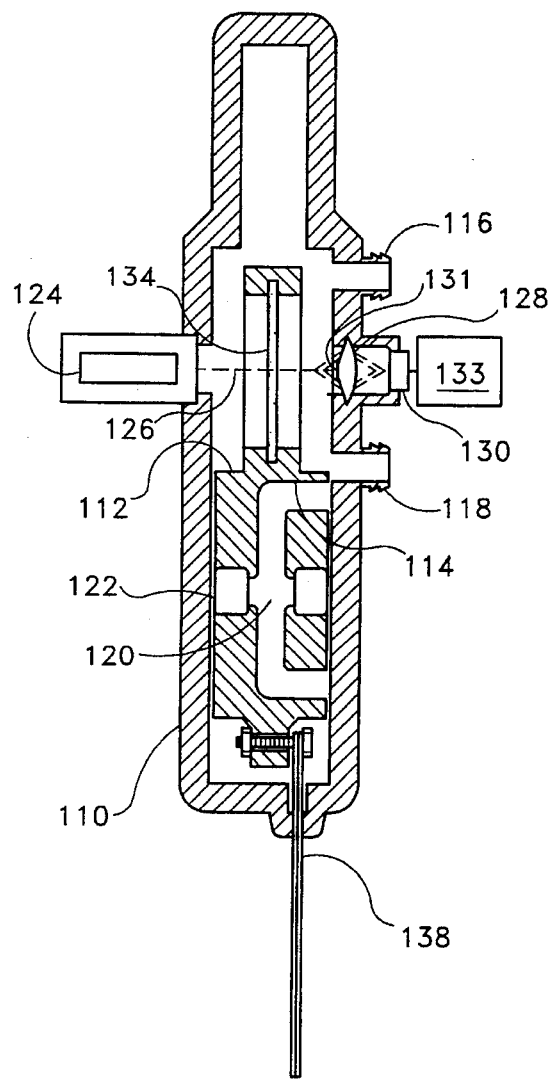
FIG. 4 is a schematic section view through the embodiment of FIG. 3 during system calibration.

A second embodiment of the apparatus is shown in the operating mode in FIG. 3 and the calibration mode in FIG. 4. Here, housing 110 is elongated and carries a movable body 112 through which conduit 114 passes. In the operating mode of FIG. 3, conduit 114 is connected to inlet 116 and outlet 118. A light beam from light source 124 passes through transparent center section 120 of conduit 114, through transparent aluminum oxide block 122, through the fluid stream in conduit 114, through condensing lens 128 to photo detector 130. Light scattered by particles in the fluid are condensed by lens 128 onto photodetector 130, typically a photodiode as discussed above, forming a characteristic pattern. These patterns are compared with pre-established acceptable patterns stored in the memory of a computer 133 or the like. When it is desired to recalibrate the system, a gas such as air is blown through conduit 114 (as discussed below) to dry the conduit, then body 112 is moved downwardly by a rod pulled by a conventional adjustable solenoid (not shown). A transparent slide 134 bearing a standard particle array is secured at the top end of body 112 and moves downwardly therewith. Eventually, transparent slide 134 passes through light beam 126, producing a scatter pattern on photo detector 130 corresponding to the standard particle pattern and number in slide 134. This standard pattern is then used, for example, and not by way of limitation, by a computer 133 or the like to re-establish a standard memory to compensate for any changes in the detection system due to temperature, equipment drift or the like. Preferably, slide 134 is drawn downwardly at a rate corresponding to the rate of fluid flow through conduit 114 in the operating mode of FIG. 3. After calibration is complete, body 112 is returned to the operating position of FIG. 3 and fluid monitoring continues.

Figure 5:
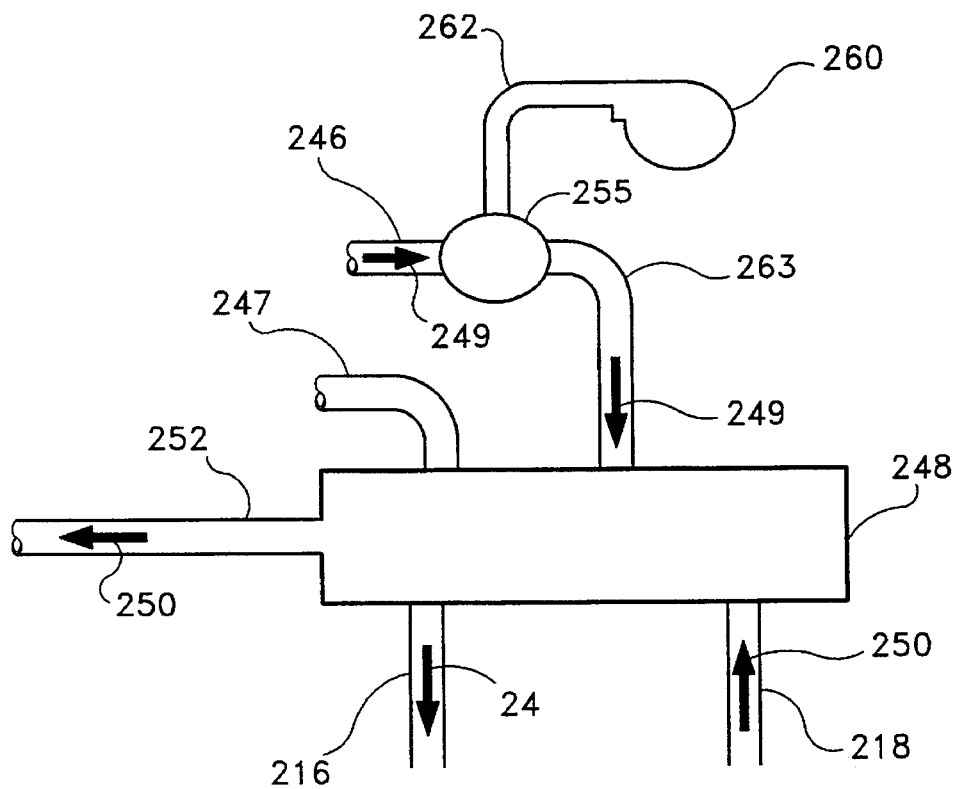
FIG. 5 is a schematic diagram of the fluid flow system of this invention during filter affluent monitoring.
Figure 6:
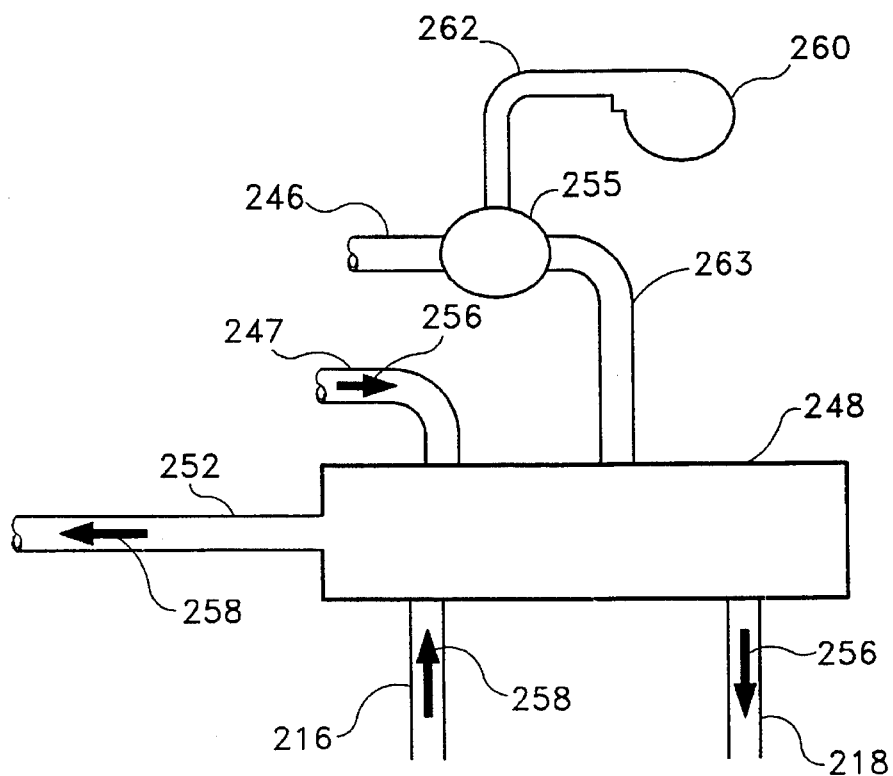
FIG. 6 is a schematic diagram of the fluid flow system as in FIG. 5, but during filter influent flow in a reverse direction.

FIGS. 5 and 6 show a schematic representation of the fluid flow system as used to monitor a liquid affluent flow 246 from a filtered line and to compare the particle concentration and sizes to a liquid flow 247 from an unfiltered line (corresponding to the filter inlet, or influent). In either case, the fluid flows through conduit 14 (FIGS. 1 and 2) or conduit 114 (FIGS. 3 and 4) with connection 216 connected to connection 16 or 116 and connection 218 connected to connection 18 or 118, respectively. During monitoring as shown in FIGS. 1 and 3, particle bearing fluid 246 passes through a three-way solenoid valve 255 and is directed by five-way solenoid valve 248 as shown in FIG. 5, into connection 216, as indicated by arrows 249 thence through the monitoring apparatus described above. After passing through the transparent section for monitoring, the liquid exits as indicated by arrow 250 and passes out through waste line 252.

For determination of filter efficiency, unfiltered filter influent is monitored by directing fluid flow as shown in FIG. 6. Liquid enters through line 247 as indicated by arrow 256, through appropriate valves in five-way valve 248 and through connection 218 to connection 18 (FIG. 1) or connection 118 (FIG. 3). After passing through the monitoring section in a reverse direction, the liquid exits through waste line 252 as indicated by arrows 258. This reverse flow will also serve to clean any particles caught in corners or eddies.

In order to fully clean the transparent section of conduit 14 or 114, it is beneficial to direct high pressure air from air compressor 260 through line 262, three-way valve 255, line 263, five-way valve 248, outlet 218, conduit 14, connection 216 and waste line 256. This air blast will also be useful in clearing any jams formed by excessive numbers of particles or the like. This air path will also be used to dry conduit 114 just before moving body 112 from the operating mode position of FIG. 3 to the calibration position of FIG. 4.

Other applications, variations and ramifications of this invention will occur to those skilled in the art upon reading this disclosure. Those are intended to be included within the scope of this invention, as defined in the appended claims.

I claim:

1. Apparatus for determining selected physical characteristics of particles in a fluid stream which comprises:

a conduit;

means for directing a fluid carrying a plurality of particles through said conduit at a predetermined rate of flow;

a transparent section along said conduit;

means for directing a narrow beam of light through said transparent section and any fluid therein;

light detection means including means for receiving light scattered by particles in any fluid in said transparent section, said received light being indicative of particle characteristics;

transparent slide means bearing a standard particle array;

means for moving said transparent slide means at a rate corresponding to said selected fluid flow rate; and means for directing said narrow beam of light through said transparent slide means to a light receiving means positioned to receive light scattered by said standard particle array.

2. The apparatus according to claim 1 wherein said light detection means comprises a single light detector and said apparatus includes means for moving said fluid conduit out from the path of said light beam between said light directing means and said light detector means and said means for moving said transparent slide moves said slide along a path across the light path between said light directing means and said single light detector.

3. The apparatus according to claim 1 wherein said light detection means comprises two light detectors and said apparatus includes reflector means movable into the path of light between said light directing means and said transparent section and reflecting that light toward a second light detector positioned such that said transparent slide moving means moves said transparent slide through the reflected light path adjacent to said second light detector.

4. The apparatus according to claim 1 wherein said means for directing a narrow beam of light is a laser emitter.

5. The apparatus according to claim 1 wherein said means for moving said transparent slide means comprises a solenoid.

6. The apparatus according to claim 1 wherein said means for receiving light is at least one photodiode.

7. The apparatus according to claim 6 further including a condensing lens adjacent to said photodiode.

8. The apparatus according to claim 1 further including means for directing a second fluid through said conduit.

9. The apparatus according to claim 1 further including means for directing pressurized gas through said conduct in a direction opposite to the particle carrying fluid to clean said conduit.

10. Apparatus for determining selected physical characteristics of particles in a fluid stream which comprises:

a conduit;

means for directing a fluid carrying a plurality of particles through said conduit in a first direction at a predetermined rate of flow;

a transparent section along said conduit;

means for directing a narrow beam of light through said transparent section and any fluid therein;

first light detection means for receiving light scattered by particles in any fluid in said transparent section, said received light being indicative of particle characteristics;

light deflecting means adjacent to said narrow beam of light, movable from a first position allowing said light beam to pass to said first light detection means to a second position at which said light is directed to a second light detection means without passing through said transparent section;

transparent slide means bearing a standard particle array movably positioned adjacent to said second light detection means to receive the deflected light beam; and means for moving said transparent slide past said second light detection means at a speed corresponding to the rate of fluid flow through said conduit.

11. The apparatus according to claim 10 wherein said means for directing a narrow beam of light is a laser emitter.

12. The apparatus according to claim 10 wherein said means for moving said transparent slide means comprises a solenoid.

13. The apparatus according to claim 10 wherein said means for receiving light is at least one photodiode.

14. The apparatus according to claim 13 further including a condensing lens adjacent to said photodiode.

15. The apparatus according to claim 10 further including means for directing a second fluid through said conduit.

16. The apparatus according to claim 10 further including means for directing pressurized gas through said conduct in a direction opposite to the particle carrying fluid to clean said conduit.

17. Apparatus for determining selected physical characteristics of particles in a fluid stream which comprises:

a conduit formed in a movable body;

means for directing a fluid carrying a plurality of particles through said conduit at a predetermined rate of flow;

a transparent section along said conduit;

means for directing a narrow beam of light through said transparent section and any fluid therein;

light detection means including means for receiving light scattered by particles in any fluid in said transparent section, said received light being indicative of particle characteristics;

means for moving said transparent section and said movable body out of the optical path of said beam of light;

transparent slide means bearing a standard particle array secured to said body to move therewith so that said transparent slide moves across said light beam after said body has moved out of said light beam; and means for moving said transparent slide across said light beam at a rate corresponding to the rate of flow of said fluid through said conduit when said transparent section is aligned with said light beam;

whereby the light scattering produced by said standard particle array and detected by said light detection means as said transparent slide moves across said light beam is useful for calibrating said light detection means when detecting scattering from particles in said fluid.

18. The apparatus according to claim 17 wherein said means for directing a narrow beam of light is a laser emitter.

19. The apparatus according to claim 17 wherein said means for moving said transparent slide means comprises a solenoid.

20. The apparatus according to claim 17 wherein said means for receiving light is at least one photodiode.

21. The apparatus according to claim 20 further including a condensing lens adjacent to said photodiode.

22. The apparatus according to claim 17 further including means for directing a second fluid through said conduit.

23. The apparatus according to claim 17 further including means for directing pressurized gas through said conduct in a direction opposite to the particle carrying fluid to clean said conduit.

24. The apparatus according to claim 17 further including means for preventing said fluid from contacting said transparent slide during movement of said transparent slide through said light beam.

25. The method of measuring selected physical characteristics of particles in a fluid stream which comprises the steps of:

directing a fluid carrying a plurality of particles through a conduit in a body at a predetermined rate of flow;

providing a transparent section in said conduit;

directing a narrow beam of light through said transparent section and the fluid therein;

detecting light scattered by particles in said fluid, said detected light being indicative of particle characteristics;

moving a transparent slide bearing a standard particle array at a rate corresponding to the rate of fluid flow;

directing said narrow beam of light through said transparent slide;

detecting light scattered by said standard particle array; and using the results of said detection Of light scattered by said standard particle array in calibrating said detection of light scattered by said particles entrained in said fluid.

26. The method according to claim 25 wherein said beam of light is directed through said transparent slide by moving said body and conduit away from said light beam and moving said transparent slide across said light beam.

27. The method according to claim 25 wherein said beam of light is directed through said transparent slide by moving a mirror into said light beam to deflect said beam and moving said transparent slide across said deflected beam adjacent to a second light detecting means.

28. The method according to claim 25 further including directing a second liquid through said conduit for comparison of particle count with said first fluid.

29. The method according to claim 25 including the further step of directing a stream of gas through said conduit to clean said conduit.

* * * * *